(12) United States Patent
Shreve et al.

(10) Patent No.: US 9,381,447 B2
(45) Date of Patent: Jul. 5, 2016

(54) FORCE BALANCE NEEDLE VALVE PRESSURE REGULATOR FOR CARBON DIOXIDE BASED CHROMATOGRAPHY

(71) Applicant: Waters Technologies Corporation, Milford, MA (US)

(72) Inventors: Joshua A. Shreve, Franklin, MA (US); Paul Linderson, Warwick, RI (US); John Maillet, Jr.; John Angelosanto, North Attleboro, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 117 days.

(21) Appl. No.: 14/381,975

(22) PCT Filed: Mar. 7, 2013

(86) PCT No.: PCT/US2013/029543
§ 371 (c)(1),
(2) Date: Aug. 28, 2014

(87) PCT Pub. No.: WO2013/134478
PCT Pub. Date: Sep. 12, 2013

(65) Prior Publication Data
US 2015/0047500 A1    Feb. 19, 2015

Related U.S. Application Data

(60) Provisional application No. 61/607,935, filed on Mar. 7, 2012.

(51) Int. Cl.
*B01D 15/10* (2006.01)
*G01N 30/32* (2006.01)
*B01D 15/16* (2006.01)
*B01D 15/40* (2006.01)
*G05D 16/20* (2006.01)

(52) U.S. Cl.
CPC .............. *B01D 15/163* (2013.01); *B01D 15/10* (2013.01); *B01D 15/40* (2013.01); *G01N 30/32* (2013.01); *G05D 16/2013* (2013.01); *G01N 2030/328* (2013.01)

(58) Field of Classification Search
CPC ...... B01D 15/10; B01D 15/163; B01D 15/40; G01N 30/32; G01N 2030/328; G05D 16/2013; G05D 16/202
See application file for complete search history.

(56) References Cited

U.S. PATENT DOCUMENTS 3,848,806 A    11/1974  Samuelsen et al.
4,032,445 A    6/1977   Munk
(Continued)

OTHER PUBLICATIONS

Guiochon G, et al., Fundamental challenges and opportunities for preparative supercritical fluid chromatography. J Chromatogr A. Feb. 25, 2011;1218(8):1037-114.

(Continued)

*Primary Examiner* — Robert Clemente
(74) *Attorney, Agent, or Firm* — McCarter & English, LLP; Deborah M. Vernon

(57) ABSTRACT

Exemplary embodiments of the present disclosure relate to systems and methods comprising a dynamic pressure regulator and a force balance needle that regulate pressure changes due to flow or composition changes in a pressurized flow system, such as, for example, a $CO_2$-based chromatography system.

15 Claims, 8 Drawing Sheets

(56) References Cited

U.S. PATENT DOCUMENTS

| | | | |
|---|---|---|---|
| 4,175,585 A | 11/1979 | Boehme | |
| 4,984,602 A | 1/1991 | Saito et al. | |
| 5,088,467 A | 2/1992 | Mesenich | |
| 5,694,973 A | 12/1997 | Chordia | |
| 8,915,261 B2 * | 12/2014 | Kanomata | B01D 15/40 137/486 |
| 2004/0112992 A1 | 6/2004 | Liskow | |
| 2007/0056357 A1 | 3/2007 | Ruegenberg et al. | |

OTHER PUBLICATIONS

International Search Report for PCT/US2013/29543 date of mailing May 23, 2013.

* cited by examiner

FORCE BALANCE NEEDLE VALVE PRESSURE REGULATOR FOR CARBON DIOXIDE BASED CHROMATOGRAPHY

RELATED APPLICATIONS

This application is a National Stage Application of International Application No. PCT/US2013/029543, filed Mar. 7, 2013, which claims priority to U.S. Provisional Application No. 61/607,935, filing date Mar. 7, 2012. Each of the foregoing applications is incorporated herein by reference in its entirety.

FIELD OF THE TECHNOLOGY

The present disclosure relates to systems and methods utilizing a dynamic back pressure regulator and a force balance needle that regulates pressure changes due to flow or composition changes in a pressurized flow system, such as, for example, a $CO_2$-based chromatography system.

BACKGROUND

Chromatographic techniques are important tools for the identification and separation of complex samples. The basic principle underlying chromatographic techniques is the separation of a mixture into individual components by transporting the mixture in a moving fluid through a retentive media. The moving fluid is typically referred to as the mobile phase and the retentive media is typically referred to as the stationary phase. The separation of the various constituents of the mixture is based on differential partitioning between the mobile and stationary phases. Differences in components' partition coefficient result in differential retention on the stationary phase, resulting in separation.

Conventionally, the methods of choice for chromatographic separations have been gas chromatography (GC) and liquid chromatography (LC). One major difference between GC and LC is that the mobile phase in GC is a gas, whereas the mobile phase in LC is a liquid. For example, in GC, a supply of inert carrier gas (mobile phase) is continually passed as a stream through a heated column containing porous sorptive media (stationary phase). A sample of the subject mixture is injected into the mobile phase stream and passed through the column, where separation of the mixture is primarily due to the differences in the volatile characteristics of each sample component at the temperature of the column. A detector, positioned at the outlet end of the column, detects each of the separated components as they exit the column. Although GC is typically a sensitive method of analysis, the high temperatures required in GC make this method unsuitable for high molecular weight biopolymers or proteins (heat will denature them), frequently encountered in biochemistry.

Conversely, LC is a separation technique in which the mobile phase is a liquid and does not require volatilization of the sample. Liquid chromatography that generally utilizes small packing particles and moderately high pressure is referred to as high-performance liquid chromatography (HPLC); whereas liquid chromatography that generally utilizes very small packing particles and high pressure is referred to as ultra-high performance liquid chromatography (UHPLC). In HPLC and UHPLC the sample is forced by a liquid at high pressure (the mobile phase) through a column that is packed with a stationary phase composed of irregularly or spherically shaped particles, a porous monolithic layer, or a porous membrane.

Because LC uses liquid as the mobile phase, LC techniques are capable of analyzing higher molecular weight compounds and, in some cases, LC can be used to prepare large scale batches of purified protein(s). However, in contrast, GC techniques are typically more sensitive and readily allow for the separation of single chiral materials. Thus, GC has conventionally been used to isolate and determine the relative purity of a chiral compound, e.g., by determining the enantiomeric excess (% ee) or the diastereomeric excess (% de) of a particular sample. As with most chromatographic techniques, the limiting factor in both GC and LC has been the ability to obtain and/or reproduce pure sample separations, each of which are typically dependent on the apparatus, methods, and conditions employed, e.g., flow rate, column size, column packing material, solvent gradient, etc.

Supercritical Fluid Chromatography is another chromatographic technique, which has typically been used in preparative applications. For every liquid substance there is a temperature above which it can no longer exist as a liquid, no matter how much pressure is applied. Likewise, there is a pressure above which the substance can no longer exist as a gas no matter how much the temperature is raised. These points are called the supercritical temperature and supercritical pressure, and define the boundaries on a phase diagram for a pure substance (FIG. 1). At this point, the liquid and vapor have the same density and the fluid cannot be liquefied by increasing the pressure. Above this point, where no phase change occurs, the substance acts as a supercritical fluid (SF). Thus, SF can be described as a fluid obtained by heating above the critical temperature and compressing above the critical pressure. There is a continuous transition from liquid to SF by increasing temperature at constant pressure or from gas to SF by increasing pressure at constant temperature.

The term SFC, while typically standing for Supercritical Fluid Chromatography, does not require or mean that supercritical conditions are obtained during or maintained throughout the separation. That is, columns do not have to be always operated in the critical region of the mobile phase. For example, in the event that the mobile phase includes a modifier (e.g., $CO_2$ and methanol as a modifier), the mobile phase is often in its subcritical region (e.g., a highly compressed gas or a compressible liquid rather than a supercritical fluid). In fact, as Guiochon et al note in section 2.3 of their review article entitled "Fundamental challenges and opportunities for preparative supercritical fluid chromatography" Journal of Chromatography A, 1218 (2011) 1037-1114: "It is obvious that SFC has very often been and still is run under subcritical conditions." Thus, the term SFC is not limited to processes requiring supercritical conditions.

Because SFC typically uses $CO_2$, SFC processes are inexpensive, innocuous, eco-friendly, and non-toxic. There is typically no need for the use of volatile solvent(s) (e.g., hexane). Finally, the mobile phase in SFC processes (e.g., $CO_2$ together with any modifier/additive as a SF, highly compressed gas, or compressible liquid) typically have higher diffusion constants and lower viscosities relative to liquid solvents. The low viscosity means that pressure drops across the column for a given flow rate is greatly reduced. The increased diffusivity means longer column length can be used.

SUMMARY

Exemplary embodiments of the present disclosure are directed to the use of a dynamic pressure regulator and force balance needle to minimize flow or compositional changes of a mobile phase in pressurized flow systems, such as a $CO_2$- based chromatography system. Exemplary embodiments of the present disclosure comprise a dynamic pressure regulator and a force balance needle between the drive mechanism and the system pressure. Assemblies and methods described herein can dampen the effects caused by pressure drops or pressure-related inconsistencies that may occur during introduction of a mobile phase, and/or throughout the pressure regulation of a mobile phase in a pressurized flow system, such as $CO_2$-based chromatography.

Exemplary embodiments comprise a needle valve driven by a solenoid or other type of actuator. Generally, the assemblies and methods include, for example, determining the optimal position of a needle with a regulator, such that minor differences or pressure fluctuations occurring from the combination of the internal pressure of a solenoid and the internal pressure created from the introduction of a mobile phase, are counterbalanced or compensated for by the needle. In one embodiment, the needle valve and solenoid are designed for enhanced stability and have a minimal change in force through the operating stroke (e.g., approximately 0.010 of an inches). A control signal (e.g., current) to the solenoid controls the force the solenoid applies to the needle and the pressure on the needle from mobile phase flow provides a counter force to the solenoid assembly. In one embodiment, the needle naturally finds a position such that the pressure force and the solenoid force balance, such that the pressure can be directly set by commanding a force out of the solenoid to give the desired pressure.

The exemplary methods and assemblies of the present technology provide numerous advantages. For example, by incorporating the present technology, pressure changes associated with a change in solvent (e.g., density, viscosity) or a change in flow (e.g., flow rate) are minimal. As a result, pressure is only affected by any slope in the force vs. stroke of the solenoid. In addition, the controller described herein requires little movement to accommodate a change in condition. That is, a given current provides a specific back pressure that varies only by tolerances of the actuator. As a result, a high degree of control can be achieved. Further, the force balance approach of the present technology cancels pressure changes due to flow or composition fluctuations. Thus, the present technology provides better pressure control over changing conditions (e.g., density changes of a mobile phase including $CO_2$).

In accordance with embodiments of the present disclosure, methods for controlling the pressure of a mobile phase in a chromatographic system, comprise: introducing a mobile phase through a port on a head portion of a regulator comprising a needle and a seat defining a bore, creating a first pressure located in said head portion between said port and the seat, wherein the mobile phase is restricted by a gap between the needle and an edge of the bore to create a second pressure on a portion of the needle extending into the seat; applying a control signal to a force actuator positioned to communicate with a back portion of said needle to generate an actuator force, such that said actuator force substantially counterbalances said first and second pressures on a front portion of said needle; wherein changes in said control signal result in movement of said needle to balance said actuator force and a needle tip force equal to a sum of the first pressure times a first control area and the second pressure times a second control area.

Methods in accordance with the embodiments described above can include one or more of the following features. The movement of the needle to balance the actuator force and the needle tip force is small. In some embodiments, the movement ranges between about 0.001 to about 0.05 inches. In embodiments, the force actuator provides a substantially constant force through an operating stroke. In some embodiments, the force actuator is a voice coil. In certain embodiments, the force actuator is a force balanced solenoid.

In accordance with other embodiments of the present disclosure, methods for controlling the pressure of a mobile phase in a chromatographic system include introducing a mobile phase into a head portion of a pressure regulator of the chromatographic system, the pressure regulator including a needle in communication with a force actuator to change a restrictive gap; and applying a control signal (e.g., a current) to the actuator to generate a known, substantially constant force from the force actuator and applied to the needle to set the pressure of the mobile phase exiting an outlet of the pressure regulator.

In accordance with other embodiments of the present disclosure methods for controlling the pressure of a mobile phase in a chromatographic system include introducing a mobile phase into a head portion of a pressure regulator of the chromatographic system at an inlet port, the pressure regulator including a needle in communication with a force actuator to change a restrictive gap; and applying a control signal to the actuator to generate a known, substantially constant force from the force actuator and applied to the needle to control the pressure of the mobile phase upstream of the inlet port of the pressure regulator.

Embodiments of the above methods can include one or more of the following features. In some embodiments, the force actuator provides a substantially constant force through an operating stroke. In some embodiments, the force actuator is a voice coil. In certain embodiments, the force actuator is a force balanced solenoid.

In accordance with other embodiments of the present disclosure, methods for controlling pressure within a pressure regulator system include: introducing a carrier flow through a port on a head portion of a regulator comprising a needle and a seat defining a bore; creating a first pressure located in the head portion between the port and the seat, wherein the carrier flow is restricted by a gap between the needle and an edge of the bore to create a second pressure on a portion of the needle extending into the seat; applying a control signal (e.g., current) to a force actuator positioned to communicate with a back portion of the needle to generate an actuator force, such that the actuator force substantially counterbalances the second pressures on a front portion of the needle; and wherein changes in properties of the carrier flow result in movement of the needle with respect to the seat to maintain a balance between said actuator force and a needle tip force equal to a sum of the first pressure times a first control area and a second pressure times a second control area and the movement of the needle occurs without adjusting the actuator force.

Embodiments of the above methods may further include one or more of the following features. In embodiments, the movement of the needle described herein ranges between about 0.001 to about 0.05 inches. In some embodiments, the force actuator described herein provides a substantially constant force through the operating stroke. In other embodiments, the force actuator described herein is a voice coil. In certain embodiments, the force actuator is a force balanced solenoid. In embodiments, the methods described herein may further include setting an output pressure of the carrier flow, such that the output pressure is substantially equal to the pressure generated in said head portion of the regulator.

BRIEF DESCRIPTION OF THE DRAWINGS

The foregoing and other features and advantages provided by the present disclosure will be more fully understood from the following description of exemplary embodiments when read together with the accompanying drawings, in which.

DETAILED DESCRIPTION

Figure 1:
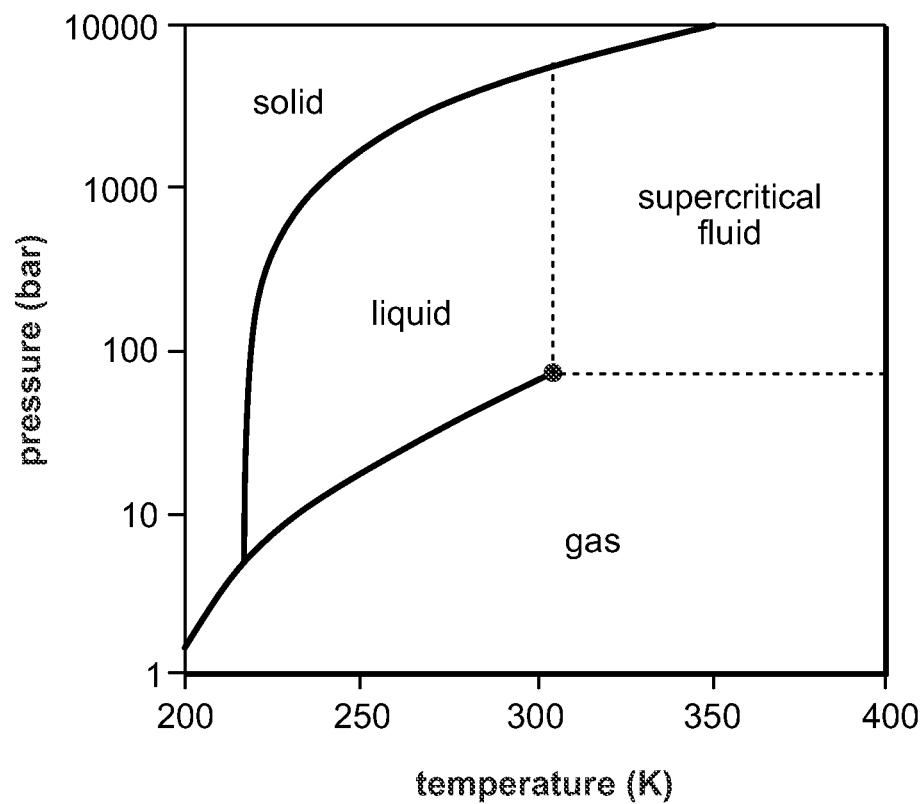
FIG. 1 is an exemplary graph of the physical state of a substance in relation to a temperature and pressure associated with the substance.

SFC can be adapted as a hybrid between HPLC and GC apparatuses, where the predominant modification is replacement of either the liquid or gas mobile phase with a supercritical fluid (or near supercritical fluid) mobile phase, such as with $CO_2$. In SFC, the mobile phase is initially pumped as a liquid or gas and is brought into the supercritical region by heating or pressurizing the mobile phase above its supercritical temperature/pressure prior to entry into a column. As the mobile phase passes through an injection valve, the sample is introduced into the supercritical stream, and the mixture is then transferred into a column. The mixture passes through the column (at supercritical or liquid state) and into the detector.

In general, the mobile phase in SFC processes have the ability to act both as substance carriers (like the mobile phases in GC), and dissolve substances readily (like the solvents used in LC). In addition to generally having lower viscosities and better diffusion profiles similar to those of certain gases, the mobile phase in SFC processes also generally have high densities and dissolving capacities similar to those of certain liquids. For example, SFs' high densities (0.2-0.5 $gm/cm^3$) provide for their remarkable ability to dissolve large, non-volatile molecules, e.g., supercritical or near supercritical $CO_2$ readily dissolves n-alkanes, di-n-alkyl phthalates, and polycyclic and aromatic compounds. Since the diffusion of solutes in a SFC mobile phase is about ten times greater than that in liquids (about three times less than in gases), this results in a decrease in resistance to mass transfer in the column and allows for fast high resolution separation. Also, the solvation strength of the mobile phase in SFC processes is directly related to the fluid density. Thus, the solubility of solids can be easily manipulated by making slight changes in temperatures and pressures.

Another important property of the mobile phase in SFC processes is that it provides high resolution chromatography at much lower temperatures. For example, an analyte dissolved in supercritical $CO_2$ can be recovered by reducing the pressure and allowing the sample to evaporate under ambient laboratory conditions. This property is useful when dealing with thermally unstable analytes, such as high molecular weight biopolymers or proteins.

The combination of one or more mechanical or column changes to an SFC instrument (e.g., a $CO_2$-based chromatography instrument) coupled with the inherent properties of the SFC itself, allows for the separation of both chiral and achiral compounds, and has become increasingly predominant in the field of preparatory separations for drug discovery and development. Despite considerable advances in SFC technology, there is a need to develop innovative methods and apparatuses that improve the use of SFC. Controlling and stabilizing the pressure in an SFC instrument by one or more process and/or improving one or more of the instrumental characteristics of the system, may lead to, amongst others, improved compound separation and efficiency.

For example, better resolution and increased flow rate would decrease cycle times (i.e., shorter cycle times) and allow for improved separation of both chiral and achiral compounds, and lead to an overall increase in laboratory efficiency; increased speed and throughput would decrease the amount of solvent and cost(s) associated with SFC; and the ability to further integrate SFC with other detection methods, such as Mass Spectrometry (MS), Flame Ionization Detectors (FID), and Ultraviolet/Visible (UV) detectors, would improve the mainstream use of SFC using a mobile phase including $CO_2$ as an eco-friendly, yet effective, alternative method for the fast, complete, and sensitive analysis of analytes.

Exemplary embodiments of the present disclosure are directed to a dynamic pressure regulator and a force balance needle that regulates pressure changes due to flow or composition changes in a pressurized flow system, such as, for example a $CO_2$-based chromatography system. Exemplary embodiments can implement one or more systems, apparatus and/or methods utilizing a dynamic pressure regulator and a force balance needle. In embodiments, the force balance needle is positioned to communicate with an actuator such that pressure variances occurring from the introduction of a mobile phase are minimized. The force balance needle naturally cancels pressure changes or fluctuations incurred by the introduction of a mobile phase. Thus, the present technology provides more consistent pressure and flow through a pressurized flow system, such as a $CO_2$-based chromatography system.

As used herein, the terms "downstream" and "upstream" refer to relative locations in a system flow, wherein upstream refers to being associated with an earlier portion of the system flow compared to a later portion of the system flow and downstream refers to being associated with a later portion of the system flow compared to an earlier portion of the system flow.

Figure 2:
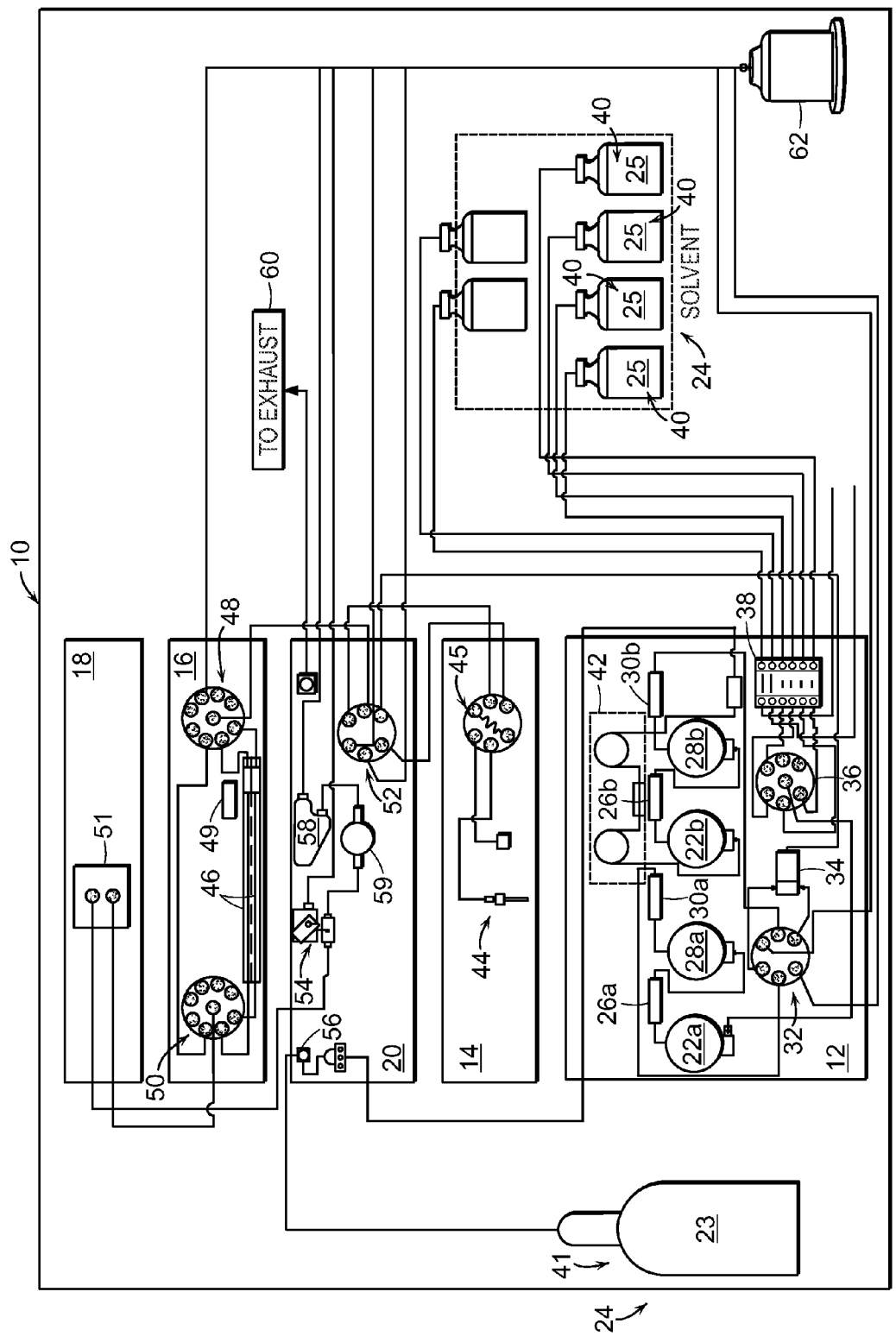
FIG. 2 is a block diagram of an exemplary pressurized flow system.

FIG. 2 is a block diagram of an exemplary pressurized flow system, which in the present embodiment is implemented as a $CO_2$-based chromatography system 10 (hereinafter "system 10). While the present embodiment is illustrative of a CO2-based chromatography system operated at or near supercritical conditions, those skilled in the art will recognize that exemplary embodiments of the present disclosure can be implemented as other pressurized flow systems and that one or more system components of the present disclosure can be implemented as components of other pressurized systems. System 10 can be configured to detect sample components of a sample using chromatographic separation in which the sample is introduced into a mobile phase that is passed through a stationary phase. System 10 can include one or more system components for managing and/or facilitating control of the physical state of the mobile phase, control of the pressure of system 10, introduction of the sample to the mobile phase, separation of the sample into components, and/or detection of the sample components, as well as venting of the sample and/or mobile phase from system 10.

Figure 3:
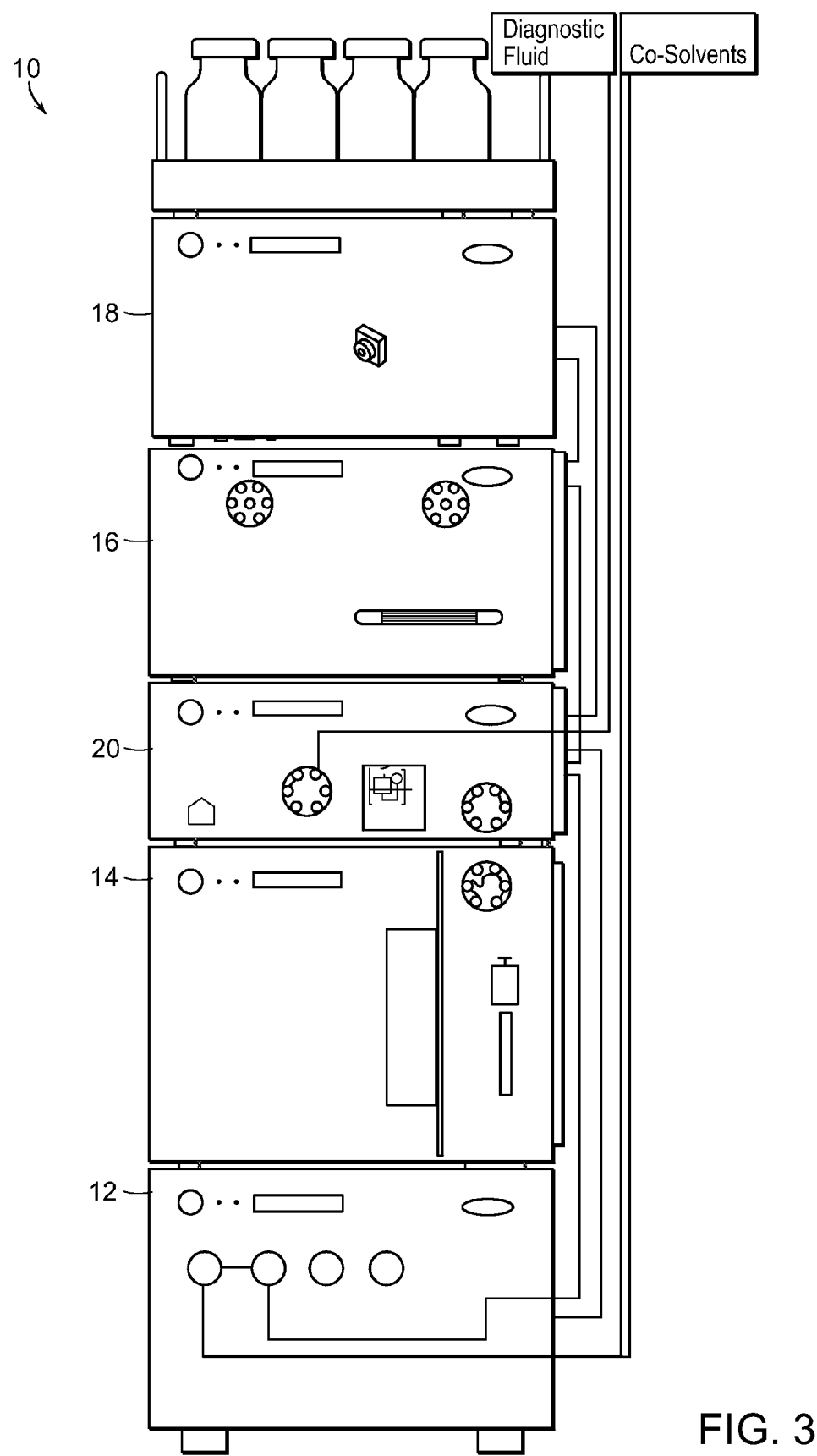
FIG. 3 is a block diagram of an exemplary arrangement of an embodiment of the system of FIG. 2.
Figure 4:
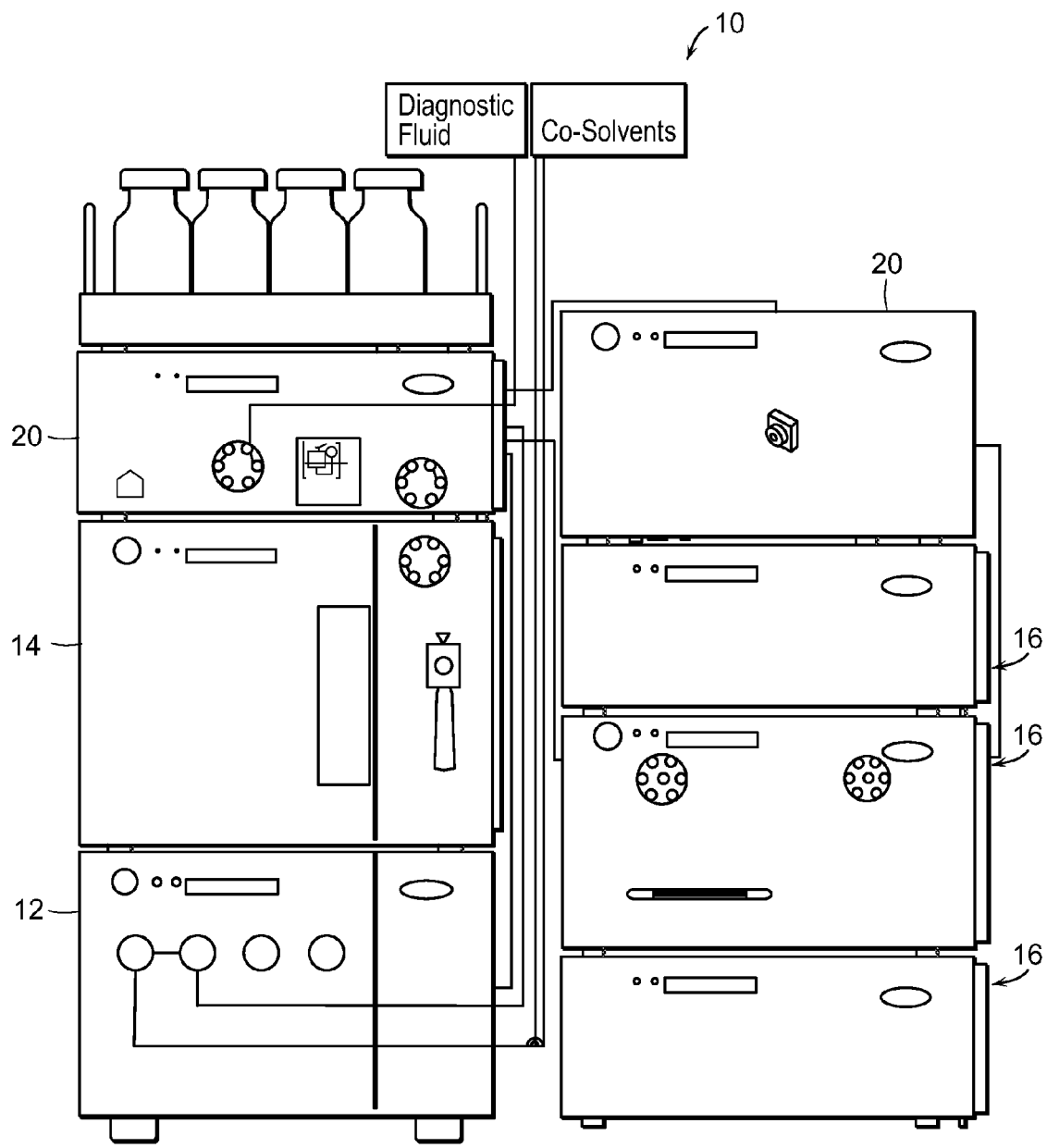
FIG. 4 is a block diagram of another exemplary arrangement of an embodiment of the system of FIG. 2.

In the present embodiment, system 10 can include a solvent delivery system 12, a sample delivery system 14, a sample separation system 16, a detection system 18 (e.g., a PDA detector), and system/convergence manager 20. In some embodiments, the system components can be arranged in one or more stacks. As one example, in one embodiment, the system components of system 10 can be arranged in a single vertical stack (FIG. 3). As another example, the system components of the system 10 can be arranged in multiple stacks (FIG. 4). Those skilled in the art will recognize that other arrangements of the components of the system 10 are possible. Furthermore, while embodiments of the system 10 have been illustrated as including system components 12, 14, 16, 18, and 20, those skilled in the art will recognize that embodiments of the system 10 can be implemented as a single integral unit, that one or more components can be combined, and/or that other configurations are possible.

The solvent delivery system 12 can include one or more pumps 22a, 22b configured to pump one or more solvents 24, such as mobile phase media 23 (e.g., carbon dioxide) and/or modifier media 25 (i.e., co-solvent, such as, e.g., methanol, ethanol, 2-methoxyethanol, isopropyl alcohol, or dioxane), through the system 10 at a predetermined flow rate. For example, the pump 22a can be in pumping communication with the modifier media 25 to pump the modifier media 25 through the system 10, and the pump 22b can be in pumping communication with the mobile phase media 23 to pump the mobile phase media 23 through the system 10. An output of the pump 22a can be monitored by a transducer 26a and an output of the pump 22b can be monitored by a transducer 26b. The transducers 26a, 26b can be configured to sense the pressure and/or flow rate associated with the output of the solvent 24 from the pumps 22a, 22b, respectively.

The outputs of the pumps 22a, 22b can be operatively coupled to an input of accumulators 28a and 28b, respectively. The accumulators 28a and 28b are refilled by the outputs of the pumps 22a and 22b, respectively, and can contain an algorithm to reduce undesired fluctuations in the flow rate and/or pressure downstream of the pumps 22a, 22b, which can cause detection noise and/or analysis errors on the system 10. An output of the accumulator 28a can be monitored by a transducer 30a and an output of the accumulator 28b can be monitored by a transducer 30b. The transducers 30a, 30b can be configured to sense pressure and/or flow rate at an output of the accumulators 28a, 28b, respectively. The outputs of the accumulators 28a, 28b can be operatively coupled to a multiport valve 32, which can be controlled to vent the solvent 24 (e.g., mobile phase media 23 and modifier media 25) being pumped by the pumps 22a, 22b and/or to output the solvent 24 to a mixer 34. The mixer 34 can mix the modifier media 25 and the mobile phase media 23 output from the pumps 22a, 22b, respectively (e.g., after first passing through the accumulators 28a, 28b) and can output a mixture of the mobile phase media 23 and the modifier media 25 to form a solvent stream (i.e., mobile phase) that flows through the system 10. The output of the mixer 34 can be operatively coupled to the system/convergence manager 20 as discussed in more detail below.

In exemplary embodiments, the solvent delivery system 12 can include a multiport solvent selection valve 36 and/or a degasser 38. The solvent selection valve 36 and/or the degasser 38 can be operatively disposed between an input of the pump 22a and solvent sources, e.g., solvent containers 40, such that the solvent selection valve 36 and/or the degasser 38 are positioned upstream of the pump 22a. The solvent selection valve 36 can be controlled to select the modifier media 23 to be used by the system 10 from one or more solvent containers 40 and the degasser 38 can be configured to remove dissolved gases from the media modifier 23 before the media modifier 23 is pumped through the system 10.

In exemplary embodiments, the solvent delivery system 12 can include a pre-chiller 42 disposed between an input of the pump 22b and a solvent source, e.g., solvent container 41, such that the pre-chiller is disposed upstream of the input to the pump 22b and downstream of the solvent container 41. The pre-chiller 42 can reduced the temperature of the mobile phase media 23 before it is pumped through the system 10 via the pump 22b. In the present embodiment, the mobile phase media 23 can be carbon dioxide. The pre-chiller can decrease the temperature of the carbon dioxide so that the carbon dioxide is maintained in a liquid state (i.e., not a gaseous state) as it is pumped through at least a portion of the system 10. Maintaining the carbon dioxide in a liquid state can facilitate effective metering of the carbon dioxide through the system 10 at the specified flow rate.

The pumps 22a and 22b can pump the solvent 24 through the system 10 to pressurize the system 10 to a specified pressure, which may be controlled, at least in part, by the system/convergence manager 20. In exemplary embodiments, the system 10 can be pressurized to a pressure between about 700 psi and about 18,000 psi or about 1,400 psi and about 8,000 psi. In one embodiment, the system 10 can be pressurized to a pressure of about 6,000 psi. By pressurizing the system 10 at these pressure levels (such as those pressure levels described above), the solvent stream (i.e., mobile phase) can be maintained in a liquid state before transitioning to a supercritical fluid state or near supercritical state (e.g., highly-compressed gas or compressible liquid) for a chromatographic separation in a column, which can be accomplished by raising the temperature of the pressurized solvent stream.

The sample delivery system 14 can select one or more samples to be passed through the system 10 for chromatographic separation and detection. The sample delivery system 14 can include a sample selection and injection member 44 and a multi-port valve 45. The sample selection and injection member 44 can include a needle through which the sample can be injected into the system 10. The multiport valve 45 can be configured to operatively couple the sample selection and injection member 44 to an input port of the system/convergence manager 20.

The sample separation system 16 can receive the sample to be separated and detected from the sample delivery system 14, as well as the pressurized solvent stream from the solvent delivery system 12, and can separate components of the sample passing through the system 10 to facilitate detection of the samples using the detection system 18. The sample separation system 16 can include one or more columns 46 disposed between an inlet valve 48 and an outlet valve 50. The one or more columns 46 can have a generally cylindrical shape that forms a cavity, although one skilled in the art will recognize that other shapes and configurations of the one or more columns is possible. The cavity of the columns 46 can have a volume that can at least partially be filled with retentive media, such as hydrolyzed silica, such as $C_8$ or $C_{18}$, or any hydrocarbon, to form the stationary phase of the system 10 and to promote separation of the components of the sample. The inlet valve 48 can be disposed upstream of the one or more columns can be configured to select which of the one or more columns 46, if any, receives the sample. The outlet valve 50 can be disposed downstream of the one or more columns 46 to selective receive an output from the one or more columns 46 and to pass the output of the selected one or more columns 46 to the detection system 18. The columns 46 can be removeably disposed between the valves 48 and 50 to facilitate replacement of the one or more columns 46 new columns after use. In some embodiments, multiple sample separation systems 16 can be included in the system 10 to provide an expanded quantity of columns 46 available for use by the system 10 (FIG. 4).

In exemplary embodiments, the sample separation system 16 can include a heater 49 to heat the pressurized solvent stream 24 prior and/or while the pressured solvent stream 24 passes through the one or more columns 46. The heater 49 can heat the pressurized solvent stream to a temperature at which the pressured solvent transition from a liquid state to a supercritical fluid state so that the pressurized solvent stream passes through the one or more columns 46 as a supercritical fluid.

Referring again to FIG. 2, the detection system 18 can be configured to receive components separated from a sample by the one or more columns 46 and to detect a composition of the components for subsequent analysis. In an exemplary embodiment the detection system 18 can include one or more detectors 51 configured to sense one of more characteristics of the sample components. For example, in one embodiment, the detectors 51 can be implemented as one or more photodiode arrays.

The system/convergence manager 20 can be configured to introduce a sample from the sample delivery system 14 into the pressurized solvent stream flowing from the solvent delivery system 12 and to pass the solvent stream and sample to the sample separation system 16. In the present embodiment, the system/convergence manager 20 can include a multiport auxiliary valve 52 which receives the sample injected by the sample delivery system 14 through a first inlet port and the pressurized solvent stream from the solvent delivery system 12 through a second inlet port. The auxiliary valve 52 can mix the sample and the solvent stream and output the sample and solvent stream via an outlet port of the multiport auxiliary valve 52 to an inlet port of the inlet valve 48 of the sample separation system 16.

The system/convergence manager 20 can also be configured to control the pressure of the system 10 and to facilitate cooling, heating and/or venting of the solvent from the system 10, and can include a vent valve 54, a shut off valve 56, a back pressure regulator 58, and a transducer 59. The vent valve 54 can be disposed downstream of the detection system 18 can be configured to decompress the system 10 by venting the solvent from the system 10 after the solvent has passed through the system 10. The shut off valve 56 can be configured to disconnect the solvent supply from the inlet of the pump 22b of the solvent delivery system to prevent the solvent from being pumped through the system 10.

The back pressure regulator 58 can control the back pressure of the system 10 to control the flow of the mobile phase and sample through the column, to maintain the mobile phase in the supercritical fluid state (or, in some embodiments, in a near supercritical state, such as, a highly-compressed gas or compressible liquid) as the mobile phase passes through the one or more columns 46 of the sample separation system 16, and/or to prevent the back pressure from forcing the mobile phase reversing its direction a flow through the one or more columns 46. Embodiments of the back pressure regulator 58 can be configured to regulate the pressure of the system 10 so that the physical state of the solvent stream (i.e., mobile phase) does not change uncontrollably upstream of and/or within the back pressure regulator 58. The transducer 59 can be a pressure sensor disposed upstream of the back pressure regulator 58 to sense a pressure of the system 10. The transducer 59 can output a feedback signal to a processing device which can process the signal to control an output of an actuator control signal from the processing device.

Figure 5:
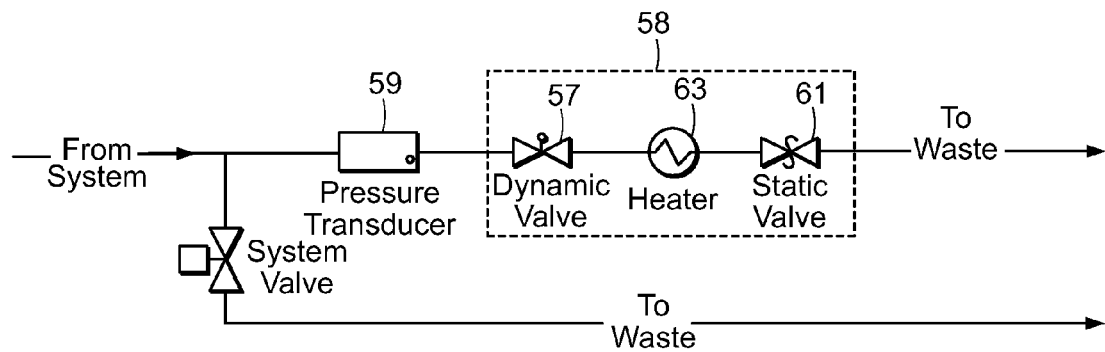
FIG. 5 is a flow diagram of a mobile phase through a system manager portion of the an exemplary embodiment of the pressurized flow system.

In exemplary embodiments, as shown in FIG. 5, the back pressure regulator 58 can include a dynamic pressure regulator 57, a static pressure regulator 61, and a heater 63. The static pressure regulator 61 can be configured to maintain a predetermined pressure upstream of the back pressure regulator 58. The dynamic pressure regulator 57 can be disposed upstream of the static pressure regulator 61 and can be configured to set the system pressure above the predetermined pressure maintained by the static regulator 61. The heater 63 can be disposed downstream of the dynamic pressure regulator 57 and can be disposed in close proximity to the static pressure regulator 61 to heat the solvent stream as it passes through the static pressure regulator 61 to aid in control of the physical state of the solvent as it passes through the static pressure regulator. The structure, function, and/or operation of the back pressure regulator 58, static pressure regulator, and/or dynamic regulator are described in more detail below.

In summary, an exemplary operation of the system 10 can pump mobile phase media 23 and modifier media 25 at a specified flow rate through the system 10 as a solvent stream (i.e., mobile phase) and can pressurize the system 10 to a specified pressure so that the solvent stream maintains a liquid state before entering the sample separation system 16. A sample can be injected into the pressurized solvent stream by the sample delivery system 14, and the sample being carried by the pressurized solvent stream can pass through the sample separation system 16, which can heat the pressurized solvent stream to transition the pressurized solvent stream from a liquid state to a supercritical fluid state. The sample and the supercritical fluid solvent stream can pass through at least one of the one or more columns 46 in the sample separation system 16 and the column(s) 46 can separate components of the sample from each other. The separated components can pass the separated components to the detection system 18, which can detect one or more characteristics of the sample for subsequent analysis. After the separated sample and solvent pass through the detection system 18, the solvent and the sample can be vented from the system 10 by the system/convergence manager 20.

In other embodiments, the system 10 described herein can also be used for preparatory methods and separations. Typical parameters, such as those described above, may be manipulated to achieve effective preparatory separations. For example, the system 10 described herein confers the benefit of exerting higher flow rates, larger columns, and column packing size, each of which contributes to achieving preparatory separation and function, while maintaining little or no variability in overall peak shape, peak size, and/or retention time(s) when compared to respective analytical methods and separations thereof. Thus, in one embodiment, the present disclosure provides $CO_2$-based chromatography systems 10, which are amendable to preparatory methods and separations with high efficiency and correlation to analytical runs.

Figure 6:
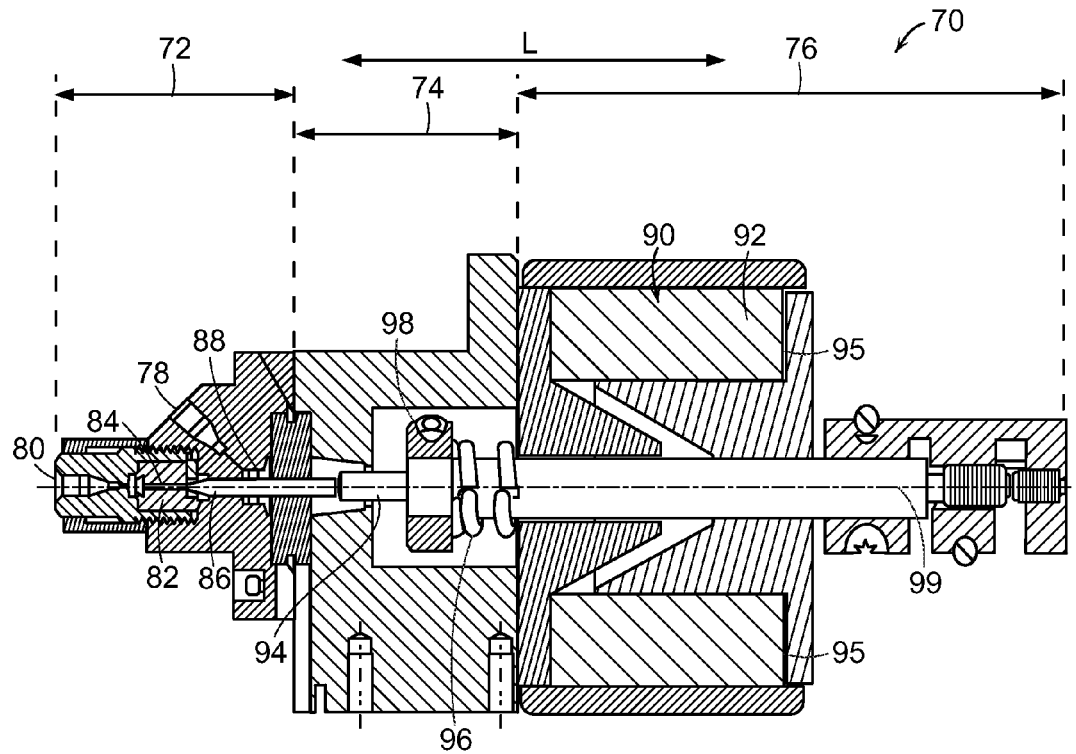
FIG. 6 is a cross-sectional view of a valve assembly for an exemplary dynamic pressure regulator in an exemplary embodiment of the pressurized system.

FIG. 6 is a cross-sectional view of an exemplary embodiment of a dynamic pressure regulator 57 along a longitudinal axis L of the dynamic pressure regulator. The dynamic pressure regulator 57 can be implemented as a valve assembly that includes a proximal head portion 72, an intermediate body portion 74, and a distal actuator portion 76. The head portion 72 of the valve assembly can include an inlet 78 to receive the pressurized solvent stream and an outlet 80 through which the pressurized solvent stream is output such that the solvent stream flows through the head portion from the inlet 78 to the outlet 80. A seat 82 can be disposed within the head portion 72 and can include a bore 84 through which the solvent stream can flow from the inlet 78 to the outlet 80 of the head.

A needle 86 extends into the head portion 72 from the body portion 74 of the valve assembly through a seal 88. A position of the needle 86 can be controlled with respect to the seat 82 to selectively control a flow of the solvent stream from the inlet 78 to the outlet 80. In exemplary embodiments, the position of the needle 86 can be used to restrict the flow through the bore 84 of the seat 82 to increase the pressure of the system 10 and can selectively close the valve by fully engaging the seat 82 to interrupt the flow between the inlet 78 and the outlet 80. By controlling the flow of the solvent stream through the head portion based on the position of the needle 86, the pressure of the system 10 can be increased or decreased. For example, the pressure of the system 10 can generally increase as the needle 86 moves towards the seat 82 along the longitudinal axis L and can generally decrease as the needle 86 moves away from the seat 82 along the longitudinal axis L.

The actuator portion 76 can include an actuator 90, such as a solenoid, voice coil, and/or any other suitable electromechanical actuation device. In the present embodiment, the actuator 90 can be implemented using a solenoid having a main body 92 and a shaft 94. The shaft 94 can extend along the longitudinal axis L and can engage a distal end of the needle 86 such that the needle 86 and shaft can form a valve member. A position of the shaft 94 can be adjustable with respect to the main body 92 along the longitudinal axis L and can be controlled by a coil (not shown) of the main body 92, which generates a magnetic field that is proportional to an electric current passing through the coil and a load applied to the shaft. The electric current passing through the coil can be controlled in response to an actuator control signal received by the actuator 90. In some embodiments, the actuator control signal can be a pulse width modulated (PWM) signal and/or the actuator control signal can be determined, at least in part, by the feedback signal of the pressure transducer 59.

The position of the shaft 94 can be used to move the needle 86 towards or away from the seat 82 to increase or decrease pressure, respectively. In exemplary embodiments, a position of the shaft 94, and therefore a position of the needle 86 with respect to the seat 82 can be controlled and/or determined based on an amount of electric current flowing through the solenoid. For example, the greater the electrical current the closer the needle 86 and shaft 94 are from the seat and the lower the pressure is in the system 10. The relationship between a position of the shaft 94 and the electric current flowing through the coil can be established through characterization of the actuator 90. The force imposed by the load on the solenoid can be proportional to the magnetic field. Similarly, the magnetic field can be proportional to the electric current (i.e., control signal) flowing through the coil of the solenoid. For embodiments in which the actuator control signal is implemented as a PWM control signal, the pressure through the pressure regulator 57 (e.g., force balance between needle 86 and shaft 94) can be set by a correlation to the duty cycle of the PWM control signal, e.g., a percentage of the duty cycle corresponding to an "on" state.

The force imposed by the actuator 90 to set the pressure through the pressure regulator 57 can be manipulated for force control purposes by inclusion of a compressed spring 96. The force imposed by the solenoid actuator 90 to position the shaft 94 can be manipulated for force control purposes by inclusion of a compressed spring 96. Spring 96 is compressed by collar 98 to apply a normalizing force to the actuator 90 through an exterior shaft liner 99. This normalizing force assists in providing a linear load (e.g., constant force) throughout the cycle of the actuator 90. In general, commercially available solenoids (i.e., solenoids not modified as described herein, e.g., without spring 96) provide a nonlinear force along their operating stroke making their use undesirable for control purposes. In addition, actuator/solenoid 90 has a negative spring rate, such that shaft 94 when the actuator 90 is in an inactive state is forced in a direction opposite of outlet 80 such that the force reduces as the solenoid stroke increases. To compensate for this force, compressed spring 96 applies a pressure to shaft 94 to counterbalance the negative spring rate of the actuator 90. In some embodiments, the spring rate selected for compressed spring 96 has a value that not only counterbalances but also applies a positive spring rate such that shaft 94 moves in a direction towards outlet 80. In addition, a shim (e.g., a non-magnetic shim, such as, for example, a plastic shim, a non-magnetic metal shim, or a void) is positioned within the main body 92 to create a distance or gap 95 for minimization of force variation purposes (e.g., to further generate a near constant force from the solenoid). That is, gap 95 prevents the actuator 90 from a completely closed state. Gap 95 is to account for an initial nonlinear force region within the solenoid's stroke (i.e., a portion of the stroke adjacent to the completely closed state in which the force generated is far from linear). The gap 95 removes the effects of the highly nonlinear region (e.g., region adjacent to the completely closed state) from the solenoid's stroke for control purposes. To determine the spring rate of the compressed spring 96 and the gap 95 distance, the solenoid is first characterized so that the appropriate springs (e.g., value of spring rate constant of the spring to normalize force in an operating region) and gap distance/thickness of shim 95 (e.g., a beginning portion or distance of the solenoid stroke that provides a nonlinear force response) can be selected to provide a substantially constant or near constant force from a solenoid.

Figure 7:
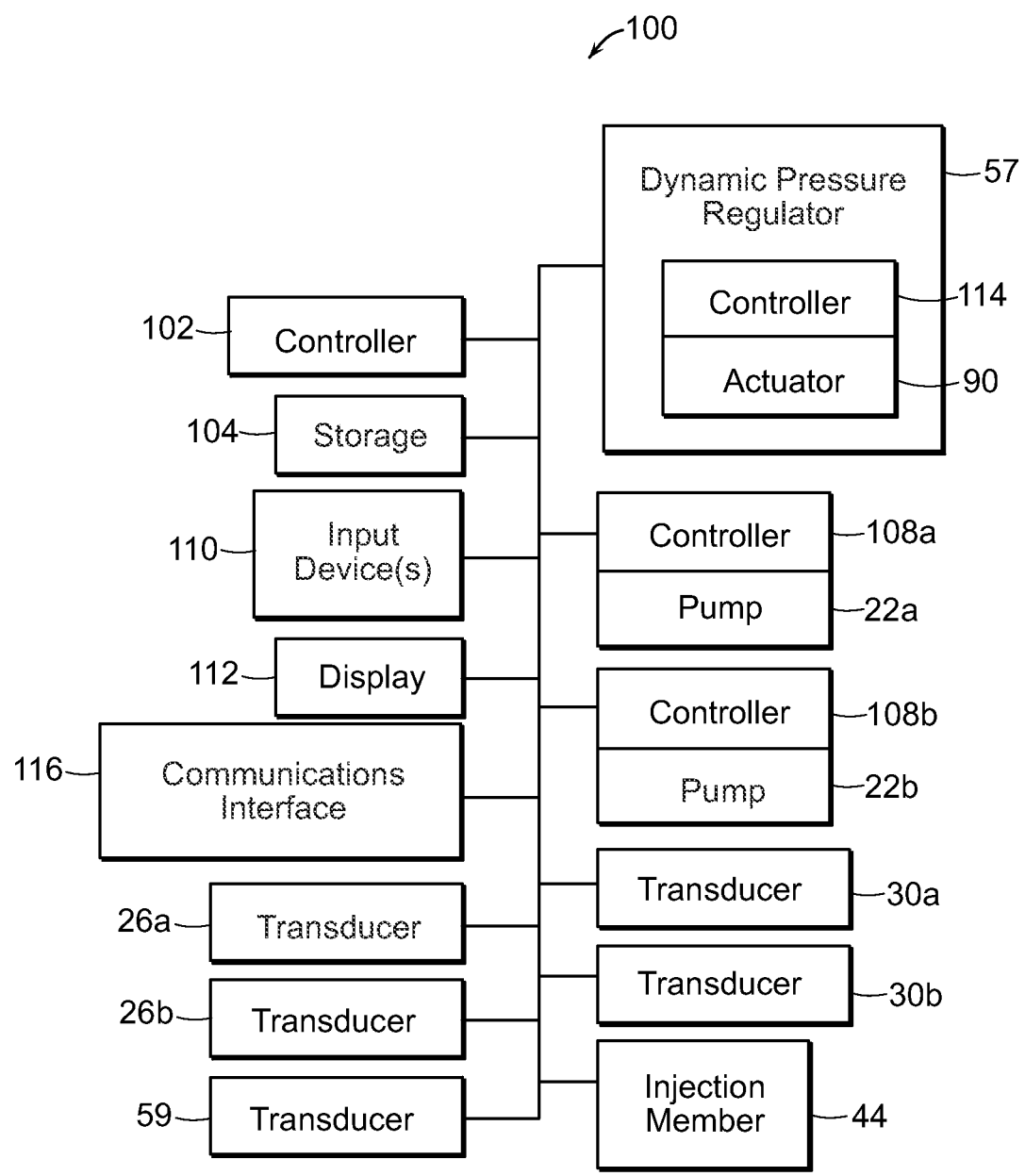
FIG. 7 is a block diagram of an exemplary control system that can be implemented to control an operation of an exemplary embodiment of the pressurized flow system.

FIG. 7 is a block diagram of an exemplary control system 100 that can be implemented to control the pressure of the system 10. The control system 100 can include a controller 102 in electrical communication with a storage device 104 (e.g., memory and/or other computer-readable storage mediums). The controller 102 can be implemented as a microcontroller, microprocessor, field programmable gate array (FPGA), and/or other processing devices. The storage 104 can be implemented as non-transitory computer readable medium including, for example, magnetic storage disks, optical disks, flash or solid state storage, and/or any other non-volatile or volatile storage medium including random access memory, such as DRAM, SRAM, EDO RAM, MRAM, and the like. The storage 106 can store information corresponding to the $CO_2$-based chromatography system 10 and/or components thereof. The storage 106 can also store instructions that are executable by the controller 102 to control an operation of system 10 including an operation of the dynamic back pressure regulator 57. The controller 102 can also be in communication with one or more of the pumps 22a, 22b, one or more of the transducers 26a, 26b, 30a, 30b, 59, the injection member 44, the dynamic pressure regulator 57, input devices 110, and/or a display 112. In this embodiment, the pumps, 22a, 22b can be associated with pump controllers 108a, 108b, respectively, and the actuator 90 of the dynamic pressure regulator 57 can be associated with an actuator controller 114.

The controller 102 can receive signals from and/or transmit signals to the transducers 26a, 26b, 30a, 30b, 59, the injection member 44, the pump controllers 108a, 108b, one or more input devices 110, such as a keyboard, mouse, or other suitable input devices, the display 112, and the actuator controller 114, and/or other devices, such as other controllers (e.g., processing devices), computing devices (e.g., a Laptop, PC, mainframe), networked devices (e.g., servers, databases), and the like, which can be communicatively coupled to the controller 102 via, for example, a communication interface 116. In exemplary embodiments, the controller 102 can process the received signals and can control an operation of the pumps 22a, 22b, the injection member 44, and/or the actuator 90 in response to the signals.

Figure 8:
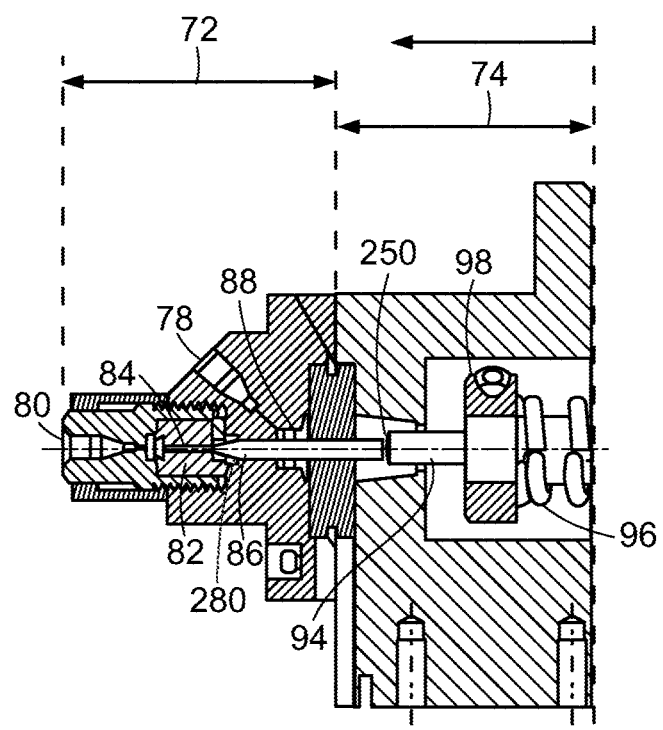
FIG. 8 represents an exemplary embodiment of a portion of FIG. 6, which is a cross-sectional view of a portion of the dynamic pressure regulator.

The pressure of system 10 is dynamically regulated in the back pressure regulator 57. FIG. 8 illustrates and embodiment of the proximal head portion 72 as described above and shown in FIG. 6. According to an embodiment of the present disclosure, a mobile phase, such as $CO_2$ enters the head portion through inlet 78, thereby creating a first pressure in the head portion 72 between the inlet 78 and the seat 82. The mobile phase is restricted by a gap between the needle 86 and the seat 82, and as a result, a second pressure is created on a front portion of the needle 280. The actuator (e.g., an unmodified solenoid, a force balanced solenoid, such as a commercially available solenoid modified with compression spring 96 shown in FIG. 6 or a voice coil) applies a constant force through shaft 94 to the back portion of the needle 250 needle 86 such that the needle is set to an appropriate location with respect to seat 82 to create the pressure entered through controller 102.

Upon disruptions, changes in control signals to the actuator, or changes in the flow properties (e.g., mobile flow rate, density changes, or viscosity changes) from the flow entering through inlet 78, needle 86 moves to maintain a force balance between the pressure applied by the force actuator at the back portion 250 of the needle 86 and the pressures created on the forward portion of the needle 280 (i.e., the first and second pressures). To maintain the balance after a disruption or a change in condition, the needle 86 moves either further forward into seat 82 (i.e. towards outlet 84) or relaxes back (i.e. towards shaft 94) to maintain in close proximity to the actuator. This automatic movement of the needle 86 is relatively small (e.g., from about 0.001 to about 0.05 inches).

Figure 9A:
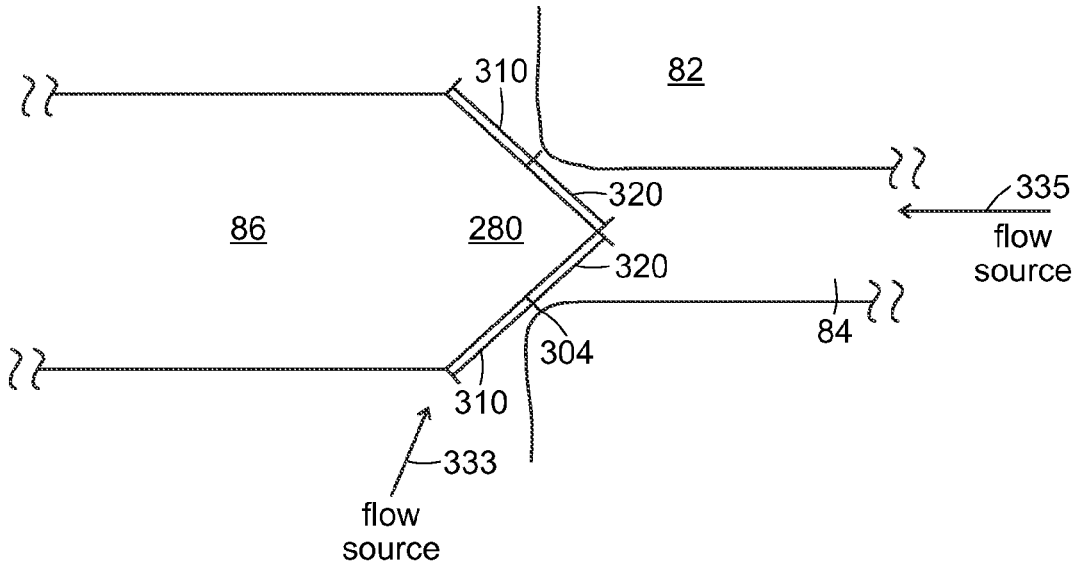
FIG. 9A is a cross-sectional view of a portion of a needle and a seat in an exemplary embodiment of a back pressure regulator.

In the embodiment discussed above, the mobile phase enters inlet port 78 and exits outlet port 80. However, in another embodiment, the mobile phase can enter port 80 and exit port 78. That is, the inlet and outlet of pressure regulator 57 are swapped. In either embodiment, pressure within the pressure regulator 57 decreases through a restrictive gap between the needle 86 and an edge 304 of the bore 84 of seat 82 as shown in FIG. 9A. Pressure acting on the needle 86 before the restriction creates an upstream pressure area and the pressure acting on the needle 86 after the restriction creates a downstream pressure area. It is noted that radial components of a pressure force acting on the needle 86 result in a zero net radial force over projected radial area. However, axially components of the pressure force on the needle 86 do not cancel out over the projected axial area, and as a result the axial components of pressure acting on the needle created by the mobile phase can be defined as a control area. For example, in an embodiment in which the pressure regulator is a back pressure regulator and port 78 is the mobile phase inlet to the pressure regulator (flow arrow 333), a first control area or an upstream control area is shown as 310 and a second control area or a downstream control area is shown as 320. The force acting on the front portion of the needle 280 can be called a needle tip force and is equal to the pressure upstream of the restrictive gap times the first control area 310 plus the pressure downstream of the restrictive gap times the second control area 320. It is further noted that changing the mobile phase inlet port from 78 to 80 would not change the operation of the back pressure regulator, but would rather change the control areas. That is, in an embodiment in which the mobile phase flow source enters from port 80 (flow arrow 335), control area 320 becomes the first control area/upstream control area and control area 310 becomes the second control area/downstream control area.

Figure 9B:
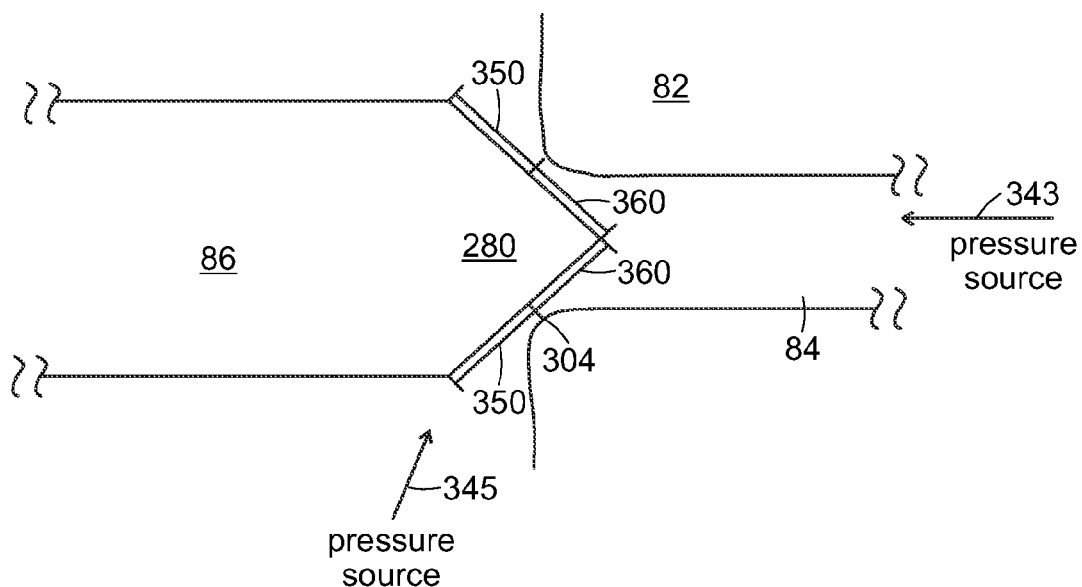
FIG. 9B is a cross-sectional view of a portion of a needle and a seat in an exemplary embodiment of a forward pressure regulator.

While the pressure regulator 57 is operating as a backpressure regulator, as described directly above, the downstream pressure is effectively constant while the upstream pressure changes with respect to the control signal sent to the actuator 90. In other embodiments, the pressure regulator 57 can be operated as a forward pressure regulator. In general, back pressure regulators are used with flow sources (however, pressure sources are possible in some embodiments) to deliver the mobile phase and control pressure between the flow source and the regulator by increasing restriction. Forward pressure regulators and flow regulators are typically used with pressure sources and control the pressure or flow downstream of the regulator by changing the flow from the pressure source by varying the restriction (e.g., gap between needle 86 and an edge 304 of the bore 84). FIG. 9B is a cross-sectional illustration of a pressure regulator operating as a forward pressure regulator in which a pressure source mobile phase inlet 80 (pressure arrow 343) forms a first control area 350 and a second control area 360. In the event that the pressure source mobile phase inlet is located at port 78 (with port 80 being the exit port) arrow 345, then the first control area is area 360 and the second control area is 350. Pressure regulator 57 and pressure regulators in accordance with the present technology, can operate as a back pressure regulator, a forward pressure regulator or a flow regulator.

When discussed from a force balance perspective, there is a balance between the force applied to the back of the needle 250 by the actuator 90 and the force applied to the forward portion of the needle 280 by the pressure coming from an inlet to the pressure regulator (i.e., needle tip force). Upon disruptions, changes in control signals to the actuator, or changes in the flow properties (e.g., mobile flow rate, density changes, or viscosity changes) from the flow entering through inlet 78, the forces become unbalanced. This is primarily controlled by the restriction created by the needle 86 to seat 82 gap (e.g., at the edge 304 of the bore 84). If the pressure rises, the force on the end of the needle increases, pushing it away from the seat; therefore reducing the restriction until the pressure created by the restriction is once again equal to the actuator force. If the pressure reduces, the force on the end of the needle decreases, and the actuator pushes it towards the seat; therefore increasing the restriction until the pressure created by the restriction is once again equal to the actuator force.

As described in the foregoing figures and disclosure, the assembly and methods herein are designed to be stable and have a minimal change in force through an operating stroke of the actuator 90. As above, a control signal (e.g., current) to the solenoid controls the force the assembly applies to the needle 86 and the pressure from the mobile phase flow through the head portion of the regulator 57 on the needle 86 provides a counter force to the solenoid assembly. The needle naturally (e.g., automatically) finds a position such that the pressure force and the solenoid force balance. Advantages of this approach include, e.g., pressure changes associated with a change in mobile phase or a change in flow is minimal, the controller requires little movement to accommodate a change in conditions, a given control signal provides specific back pressure, and the force balance approach naturally cancels pressure changes due to flow or compositional fluctuations.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component or step Likewise, a single element, component or step may be replaced with a plurality of elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other functions and advantages are also within the scope of the invention.

What is claimed is:

1. A method for controlling the pressure of a mobile phase in a chromatographic system, comprising:
    introducing a mobile phase through a port on a head portion of a regulator comprising a needle and a seat defining a bore, creating a first pressure located in said head portion between said port and the seat, wherein the mobile phase is restricted by a gap between the needle and an edge of the bore to create a second pressures on a portion of the needle extending into the seat; and
    applying a control signal to a force actuator positioned to communicate with a back portion of said needle to generate an actuator force, such that said actuator force substantially counterbalances said first and second pressures on a front portion of said needle; wherein
    changes in said control signal result in movement of said needle to balance said actuator force and a needle tip force equal to a sum of the first pressure times a first control area and the second pressure times a second control area.

2. The method of claim 1, wherein the movement of the needle ranges between about 0.001 to about 0.05 inches.

3. The method of claim 1, wherein the force actuator provides a substantially constant force through an operating stroke.

4. The method of claim 1, wherein the force actuator is selected from a voice coil or a force balanced solenoid.

5. A method for controlling the pressure of a mobile phase in a chromatographic system, comprising:
    introducing a mobile phase into a head portion of a pressure regulator of the chromatographic system, the pressure regulator including a needle in communication with a force actuator to change a restrictive gap; and
    applying a control signal to the force actuator to generate a known, substantially constant force from the force actuator and applied to the needle to set the pressure of the mobile phase exiting an outlet of the pressure regulator.

6. The method of claim 5, wherein the force actuator provides a substantially constant force through an operating stroke.

7. The method of claim 5, wherein the force actuator is selected from a voice coil or a force balanced solenoid.

8. A method for controlling the pressure of a mobile phase in a chromatographic system, comprising:
    introducing a mobile phase into a head portion of a pressure regulator of the chromatographic system at an inlet port, the pressure regulator including a needle driven by a force actuator to change a restrictive gap; and
    applying a control signal to the force actuator to generate a known, substantially constant force from the force actuator and applied to the needle to control the pressure of the mobile phase upstream of the inlet port of the pressure regulator.

9. The method of claim 8, wherein the force actuator provides a substantially constant force through an operating stroke.

10. The method of claim 8, wherein the force actuator is selected from a voice coil or a force balanced solenoid.

11. A method for controlling pressure within a pressure regulator system, comprising:
    introducing a carrier flow through a port on a head portion of a regulator comprising a needle and a seat defining a bore, creating a first pressure located in said head portion between the port and the seat, wherein the carrier flow is restricted by a gap between the needle and an edge of the bore to create a second pressure on a portion of the needle extending into the seat;
    applying a control signal to a force actuator positioned to communicate with a back portion of said needle to generate an actuator force, such that said actuator force substantially counterbalances said first and second pressures on a front portion of said needle; and
    wherein changes in properties of the carrier flow result in movement of the needle with respect to the seat to maintain a balance between said actuator force and a needle tip force equal to a sum of the first pressure times a first control area and the second pressure times a second control area, and said movement of the needle occurs without adjusting said actuator force.

12. The method of claim 11, wherein the movement of the needle ranges between about 0.001 to about 0.05 inches.

13. The method of claim 11, wherein the force actuator provides a substantially constant force through an operating stroke.

14. The method of claim 11, wherein the force actuator is selected from a voice coil or a force balanced solenoid.

15. The method of claim 11, further comprising setting an output pressure of the carrier flow, such that the output pressure is substantially equal to the pressure generated in said head portion of the regulator.

* * * * *